United States Patent [19]

Goch

[11] Patent Number: 4,653,511

[45] Date of Patent: Mar. 31, 1987

[54] MICROSAMPLE BLOOD COLLECTING DEVICE

[76] Inventor: Thomas A. Goch, R.R. #1, Box 381, Rockville, Ind. 47872; John R. Meek, 311 Dubois Street, Crawfordsville, Ind. 47933

[21] Appl. No.: 658,405

[22] Filed: Oct. 5, 1984

[51] Int. Cl.⁴ .............................................. H61B 5/14
[52] U.S. Cl. .................................. 128/763; 128/765; 128/766
[58] Field of Search ................ 128/760, 762, 763, 765, 128/766; 604/168, 256

[56] References Cited

U.S. PATENT DOCUMENTS

| | | | |
|---|---|---|---|
| 2,452,643 | 11/1948 | Fields | 604/905 |
| 2,595,493 | 5/1952 | Slaby et al. | 128/765 |
| 3,640,267 | 2/1972 | Hurtig et al. | 128/765 |
| 3,741,217 | 6/1973 | Ciarico | 604/256 |
| 4,003,262 | 1/1977 | Gerarde | 128/763 |
| 4,214,874 | 7/1980 | White | 128/763 |
| 4,215,700 | 8/1980 | Crouther et al. | 128/763 |
| 4,266,559 | 5/1981 | Akhavi | 128/766 |
| 4,373,535 | 2/1983 | Martell | 128/765 |
| 4,393,882 | 7/1983 | White | 128/763 |
| 4,416,291 | 11/1983 | Kaufman | 128/763 |

*Primary Examiner*—Edward M. Coven
*Attorney, Agent, or Firm*—Marhsall, O'Toole, Gerstein, Murray & Bicknell

[57] ABSTRACT

A microsample device for blood sample collection comprises a hypodermic needle to which is attached a mixing chamber having an enlarged bore relative to the bore of its inlet and outlet conduits, and a supply of a soluble solid anticoagulant contained within the chamber. The anticoagulant is automatically mixed with the blood sample in the mixing chamber, eliminating the need for mixing balls or other mechanical mixing elements. The exit conduit from the mixing chamber leads to a capillary tube of sufficient length to accommodate a desired blood sample. The free end of the capillary tube is provided with a hydrophobic filter which permits air to escape from the interior of the collecting device as the blood sample enters but which blocks the further flow of blood as soon as the device is filled.

7 Claims, 6 Drawing Figures

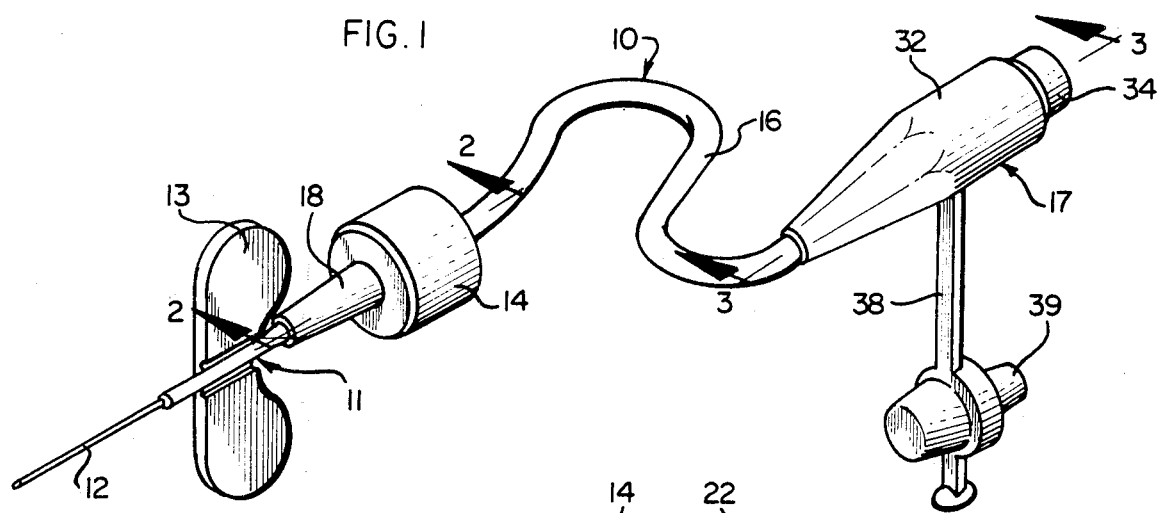
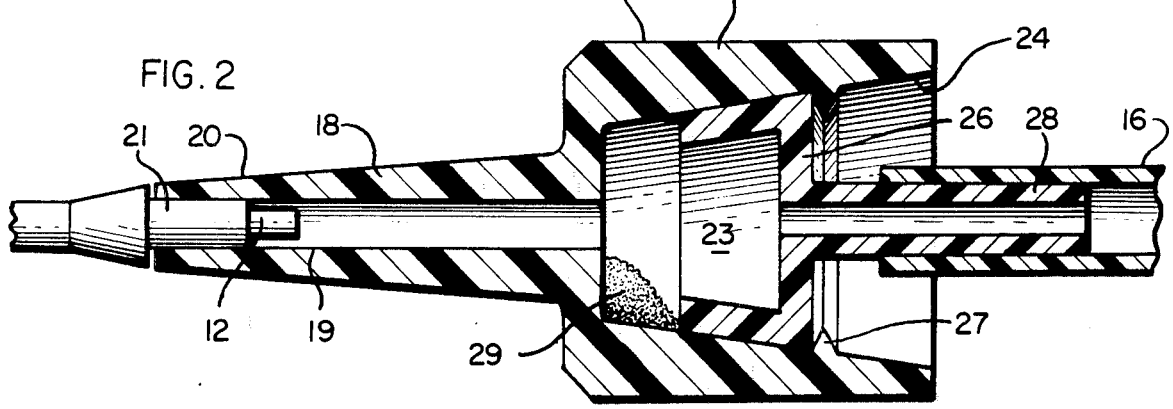
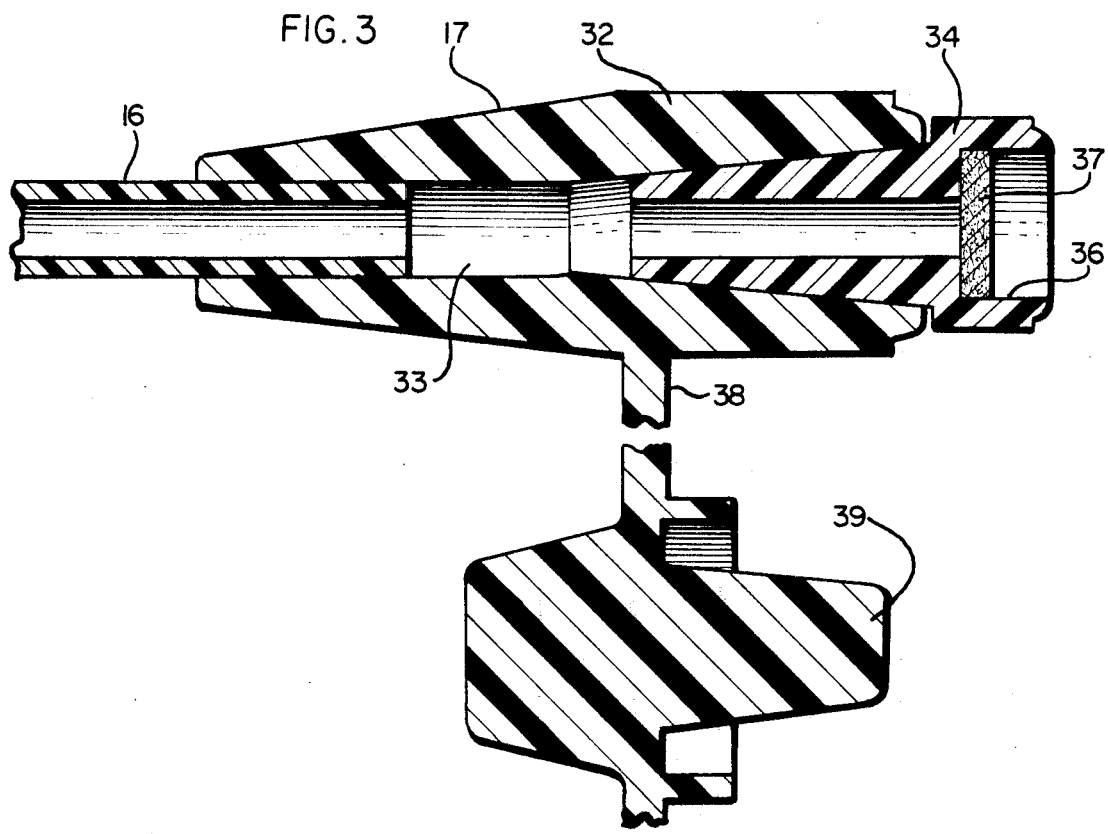

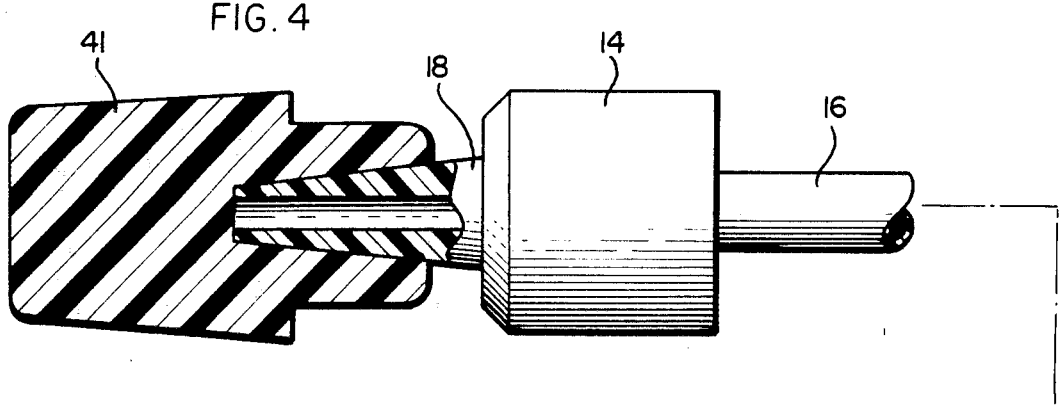
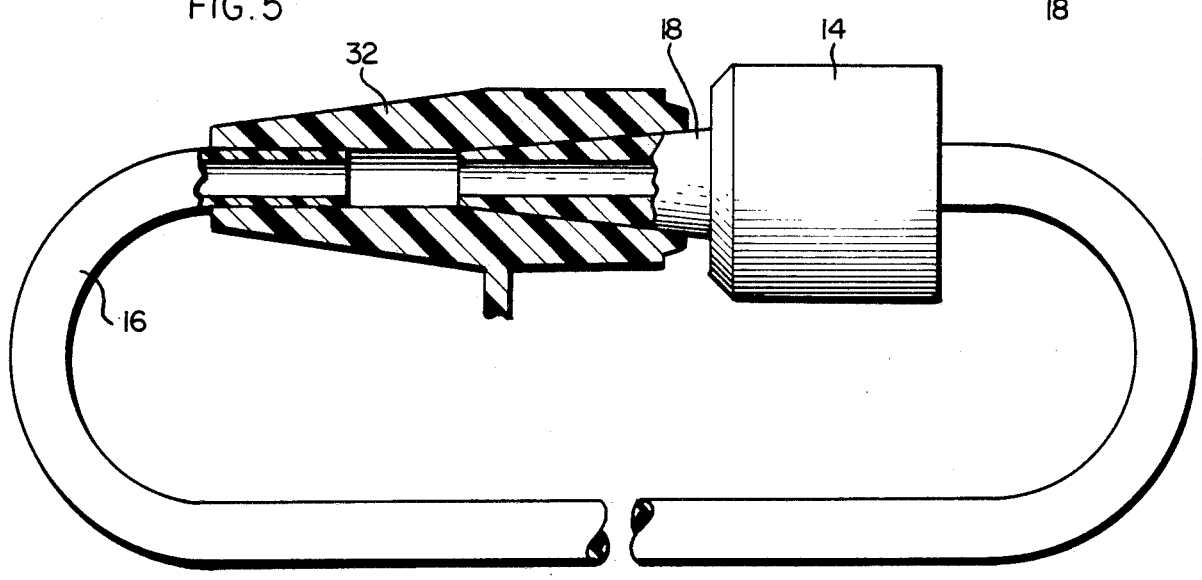
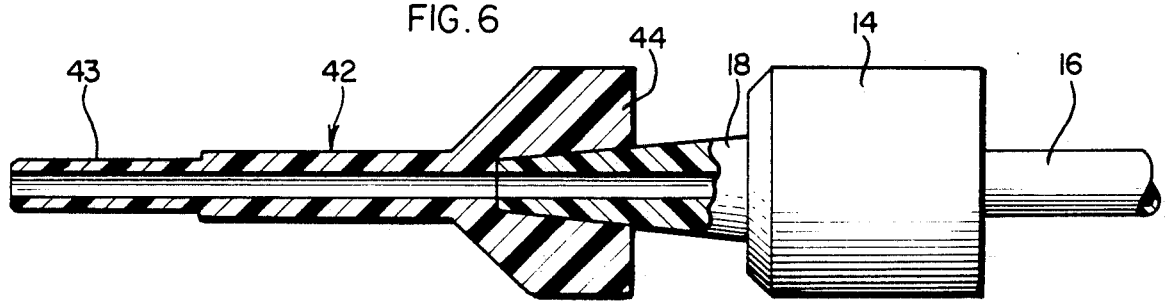

MICROSAMPLE BLOOD COLLECTING DEVICE

This invention relates to an improved device for collecting a microsample of blood for laboratory analysis.

BACKGROUND OF THE INVENTION

Conventional methods for collecting a sample of blood from a patient for laboratory analysis, such as blood gas analysis, include the use of hypodermic syringes of conventional size (1-5 cc) and capillary tubes which collect a much smaller blood sample. Regardless of the size of sample which is collected, there are certain precautions which must be observed in order to avoid erroneous analytical results, i.e., an anticoagulant must be present in the sampling device to prevent coagulation of the blood sample, and any air bubbles within the sample must be eliminated to avoid a loss of $pCO_2$.

Before taking a blood sample with a syringe of conventional size and construction, the dead space between the plunger of the syringe and the needle is typically filled with an anticoagulant solution, such as a heparin solution, to prevent entrapment of air bubbles as well as to prevent coagulation of the sample. The volume of the heparin solution, however, may be substantial relative to the volume of the blood sample, thus leading to dilution thereof and consequent reduction in $pCO_2$ values. In addition, the relatively large size of the blood sample withdrawn by the syringe may be disadvantageous when repeated samplings are necessary, or when dealing with infants.

With the availability of blood gas analyzers operable with substantially smaller blood samples (40–200 $\mu l$), microsampler devices have become available. Such devices consist essentially of a hypodermic needle attached to a capillary tube which employ no plunger as in a conventional syringe and which are pre-loaded with a solid anticoagulant, typically a salt of heparin, thereby eliminating dilution problems. Such sampling devices are filled by the arterial or veinous pressure of the patient and are therefore less likely to entrap bubbles of air. Because of the restricted cross-sectional area of the capillary tube, however, dissolution and mixing of the anti-coagulant in the blood cannot be readily accomplished by shaking the device. Mixing of the heparin with the blood sample has been accomplished by the use of mechanical agitators, e.g., a spherical steel ball enclosed within the tube or an elongated magnetic "flea" which is moved along the length of the capillary tube by means of an external magnet. The use of such mechanical agitators, however, may cause physical damage to the cells of the blood sample.

SUMMARY OF THE INVENTION

In accordance with the invention, there is provided a microsample device for blood sample collection incorporating a solid anticoagulant, in which the necessity for a mixing ball or magnetic flea is eliminated, mixing of the anticoagulant with the blood sample occurring automatically as the collecting device is filled. The device of the invention comprises a hypodermic needle to which is attached a mixing chamber having an enlarged bore relative to the bore of its inlet and outlet conduits, and a supply of a soluble solid anticoagulant contained within the chamber. The exit conduit from the mixing chamber leads to a capillary tube of sufficient length to accommodate a desired blood sample. The free end of the capillary tube is provided with a hydrophobic filter which permits air to escape from the interior of the collecting device as the blood sample enters but which blocks the further flow of blood as soon as the device is filled. Other features and advantages of the device of the invention will be apparent from the detailed description which follows.

BRIEF DESCRIPTION OF THE DRAWINGS

In the accompanying drawings:

FIG. 1 is a perspective view of the blood sampling device of the invention showing in order from the left a hypodermic needle assembly, a mixing chamber attached thereto, a capillary tube attached to the mixing chamber and a filter unit provided with an auxiliary seal plug;

FIG. 2 is a cross-sectional view along the line 2—2 of FIG. 1 showing the interior construction of the mixing chamber and the anticoagulant contained therein;

FIG. 3 is a sectional view along the line 3—3 of FIG. 1 showing the construction of the filter housing, filter plug, and seal plug;

FIG. 4 is a partially schematic view of the device of the invention showing a seal cap used for sealing one end of the device after removal of the hypodermic needle and the seal plug in place at the other end after removal of the filter plug;

FIG. 5 shows an alternative arrangement for sealing the sampling device, in which the tapered male end of the mixing chamber is inserted into the correspondingly tapered female end of the filter housing; and FIG. 6 shows a typical adapter attached to the tapered end of the mixing chamber and used for introducing the blood sample into an analyzer.

DETAILED DESCRIPTION

As shown in FIG. 1, the blood collecting device 10 of the invention comprises a hypodermic needle assembly 11 including a needle 12 and winged holder 13, a mixing chamber 14, a capillary tube 16, and a filter unit 17 which are interconnected for fluid flow therethrough. As shown in FIG. 2, mixing chamber 14 is provided with an inlet conduit 18 having a cylindrical bore 19, the exterior surface 20 of which has a male taper. Needle assembly 11 has a plug section 21 which is sized to be insertable in and removable from bore 19 of inlet conduit 18 and to be frictionally retained therein. If desired, the winged hypodermic needle can be replaced with a conventional hypodermic needle (not shown) having a hub provided with a female taper adapted to mate with the male taper of inlet conduit 18.

Mixing chamber 14 is provided with a generally cylindrical section 22 having a hollow interior zone 23 defined in part by an interior outwardly tapering wall 24, into which is inserted a hollow plug section 26 having a similarly tapered outer wall. An annular lug or ring 27 formed in the interior surface of cylindrical section 22 prevents displacement of plug section 26 from cylindrical section 22 during normal handling of the device. Both the cylindrical section and the plug section of mixing chamber 14 are suitably formed of a plastic material, such as polypropylene, having sufficient resiliency to permit annular ring 27 to deform sufficiently for the insertion of plug section 26. After insertion of plug section 26, it is retained in position by annular ring 27. Extending outwardly from plug section 26 is an outlet conduit 28 which is in liquid communication with interior zone 23 defined by cylindrical section 22 and plug section 26.

Located within mixing chamber 14 is a supply of a solid soluble anticoagulant 29 in an amount sufficient to prevent coagulation of the blood sample collected by the device. Anticoagulant 29 can be any material having anticoagulating properties and which is readily soluble in blood. Preferred are the alkaline earth and alkali metal salts of heparin, particularly lithium and sodium heparin, which have been lyophilized to increase their solubility. The requisite quantity of the anticoagulant depends on the size of the desired blood sample, and can be readily determined by those skilled in the art.

Attached to outlet conduit 28 of mixing chamber 14 is one end of a flexible capillary tube 16, the other end of which is attached to the inlet of a filter housing 32 having a bore 33, the outlet end of which is provided with a female taper adapted to receive a hollow filter plug 34 having a corresponding male taper. Positioned in the open end 36 of the filter plug 34 is a hydrophobic filter element 37 having a pore size large enough to pass air readily, but small enough to prevent the passage of blood therethrough. Filter plug 34 is frictionally maintained within filter housing 32 but can be removed when so desired.

Attached to filter housing 32 by a flexible connection 38 is a solid seal plug 39 having a male taper which can be inserted into the open end of filter housing 32 after the removal of filter plug 34.

The interior zone 23 of mixing chamber 14 has an effective cross-sectional area substantially larger than the corresponding cross-sectional areas of the bores of inlet conduit 18 and outlet conduit 28. Accordingly, when blood enters the mixing chamber through inlet conduit 18, zone 23 provides an increased residence time within mixing chamber 14 which is sufficient for the anticoagulant 29 contained therein to be substantially dissolved within the blood stream by the time the mixing chamber is filled. After the chamber is filled, the blood initially exiting through outlet conduit 28 contains a relatively high proportion of dissolved heparin which coats the walls of capillary tube 16. The anticoagulant within the coating on the walls rapidly diffuses into the main body of the blood sample, preventing coagulation therein without the necessity for mixing by shaking or by passing a ball or elongated flea through the capillary tube.

The restricted bore diameter of inlet conduit 18 causes the blood to enter mixing chamber 14 in the form of a jet which creates a swirling action within zone 23, further insuring the rapid dissolution of the anticoagulant contained therein. Outlet conduit 28 preferably has an inner bore smaller than the bore of the inlet conduit, thus insuring that mixing chamber will remain full of blood and that the blood stream will therefore not bypass the anticoagulant without dissolving it.

The interior volume of mixing chamber 14 is not particularly critical provided that it is sufficient in size to insure substantial dissolution of the anticoagulant before the stream of blood exits therefrom. For practical use, a mixing chamber having an inlet bore diameter of about 0.07 in., an outlet bore diameter of about 0.035 in., and an interior volume of about 40–50 $\mu$l has been found sufficient to insure adequate dissolution and mixing of heparin needed to prevent coagulation in a sample of blood as large as 700 $\mu$l. If the taking of larger samples is contemplated, the volume of the mixing chamber may appropriately be increased.

The the blood sample collecting device of the invention is used in the conventional fashion. With filter plug 34 inserted in housing 32, needle 12 is inserted into a suitable blood vessel of a patient, typically an artery, and, with the device held in a generally vertical position, blood is permitted to flow under arterial pressure until capillary tube 16 is filled and the blood reaches filter 32, whereupon flow ceases. After removal of the hypodermic needle from the patient, hypodermic needle assembly 11 is removed from inlet conduit 18 and a seal cap 41 (see FIG. 4) having a female taper is used to seal inlet conduit 18. Filter plug 34 is then removed from filter housing 32 and seal plug 39 is inserted into the open end of filter housing 32 to produce a sealed unit.

An alternative arrangement for of sealing the collecting device is illustrated in FIG. 5 and can be used when the length of capillary tube 16 is sufficiently great. As shown in FIG. 5, instead of using seal cap 41 and solid plug 39 for sealing the ends of the assembly, tapered inlet conduit 18 is inserted into the tapered open end of filter housing 32 to produce a unit which is sealed against the leakage of blood or the entry of air.

The blood sample contained within the device of the invention is introduced into a blood analyzer in conventional fashion. Typically, an adapter plug 42, having one end 43 suitable for use with the inlet of an analyzer, is provided with a female tapered section at its other end 44, into which inlet conduit 18 is inserted and the sample is injected into the analyzer by suitable means, e.g., application of a vacuum. To facilitate injection, filter plug 34 is desirably removed from its housing, or alternatively, filter 37 within filter plug 34 can be perforated by any suitable means not shown.

If for any reason a blood sample larger than the rated capacity of a given device is required, a hypodermic syringe having a standard tapered male end can be inserted into filter housing 32 after removal of filter plug 34 and the sample collected in conventional fashion by movement of the syringe plunger.

The foregoing detailed description has been given for clearness of understanding only and no unnecessary limitations should be understood therefrom, as modifications will be obvious to those skilled in the art.

What is claimed:

1. A device for collecting a micro sample of blood for laboratory analysis comprising:
    a hypodermic needle;
    a mixing chamber having an inlet conduit in fluid communication with said needle and an outlet conduit, the cross-sectional area of said chamber being substantially larger than the respective cross-sectional areas of said inlet and outlet conduit, said outlet conduit having a bore which is smaller than the bore of said inlet conduit, whereby in use of said device, said mixing chamber remains full of blood;
    an anticoagulant in said chamber in an amount sufficient to prevent coagulation of a blood sample collected in said device;
    a capillary tube having first and second ends,
    said first end of said tube being in fluid communication with said outlet conduit of said mixing chamber; and
    a hydrophobic filter in fluid communication with said second end of said capillary tube, said filter being effective to permit the escape of air from said tube while blocking the passage of blood therethrough.

2. A device in accordance with claim 1 wherein said anticoagulant is a lyophilized salt of heparin.

3. A device in accordance with claim 1 wherein the interior volume of said mixing chamber is sized to produce a residence time therein for a sample of blood being collected which is sufficient to insure substantial dissolution of said anticoagulant before said blood sample exits said chamber.

4. A device in accordance with claim 3 wherein said second end of said capillary tube is provided with a housing for said filter,
said housing having an internal bore in fluid communication with said capillary tube, said bore having an outwardly opening female taper;
said filter being contained in a hollow plug having a male taper releasably receivable in the bore of said housing.

5. A device in accordance with claim 4 further including a solid plug having a male Luer taper and flexible means attaching said solid plug to said housing,
said solid plug being sealingly insertable in said housing after removal of said hollow plug and said filter.

6. A device in accordance with claim 1 wherein said inlet conduit has a tip provided with an external male taper and a bore frictionally and releasably receiving said hypodermic needle.

7. A device in accordance with claim 6 wherein said capillary tubing is flexible and sufficiently long to permit the insertion of said tip of said inlet conduit into the bore of said filter housing, whereby the interior of said device is hermetically sealed.

* * * * *